(12) United States Patent
Schläpfer et al.

(10) Patent No.: US 6,248,105 B1
(45) Date of Patent: Jun. 19, 2001

(54) DEVICE FOR CONNECTING A LONGITUDINAL SUPPORT WITH A PEDICLE SCREW

(75) Inventors: Fridolin Schläpfer, Glarus; Martin Hess, Hölstein, both of (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/423,891

(22) PCT Filed: Jun. 16, 1997

(86) PCT No.: PCT/CH97/00236

§ 371 Date: Nov. 16, 1999

§ 102(e) Date: Nov. 16, 1999

(87) PCT Pub. No.: WO98/52482

PCT Pub. Date: Nov. 26, 1998

(51) Int. Cl.$^7$ .................................................. A61B 17/56
(52) U.S. Cl. ................................................................ 606/61
(58) Field of Search ..................................... 606/61, 60, 53

(56) References Cited

U.S. PATENT DOCUMENTS

| | | |
|---|---|---|
| 4,946,458 | 8/1990 | Harms et al. . |
| 5,176,680 | 1/1993 | Vignaud et al. . |
| 5,207,678 | 5/1993 | Harms et al. . |
| 5,261,909 | 11/1993 | Sutterlin et al. . |
| 5,352,226 | 10/1994 | Lin . |
| 5,429,639 * | 7/1995 | Judet ........................................ 606/61 |
| 5,443,467 | 8/1995 | Biedermann et al. . |
| 5,466,237 | 11/1995 | Byrd, III et al. . |
| 5,474,551 | 12/1995 | Finn et al. . |
| 5,474,555 | 12/1995 | Puno et al. . |
| 5,499,983 | 3/1996 | Hughes . |
| 5,501,684 | 3/1996 | Schlapfer et al. . |
| 5,520,689 * | 5/1996 | Schlapfer et al. ...................... 606/61 |
| 5,520,690 | 5/1996 | Errico et al. . |
| 5,527,314 | 6/1996 | Brumfield et al. . |
| 5,531,746 | 7/1996 | Errico et al. . |
| 5,536,268 * | 7/1996 | Griss ........................................ 606/61 |
| 5,549,608 | 8/1996 | Errico et al. . |
| 5,554,157 | 9/1996 | Errico et al. . |
| 5,575,791 | 11/1996 | Lin . |
| 5,575,792 | 11/1996 | Errico et al. . |

(List continued on next page.)

FOREIGN PATENT DOCUMENTS

| | | |
|---|---|---|
| 195 09 332 C1 | 8/1996 | (DE) . |
| 0 242 708 | 10/1987 | (EP) . |
| 0 330 881 A1 | 9/1989 | (EP) . |
| 0 441 729 A1 | 8/1991 | (EP) . |
| WO 94/00066 | 1/1994 | (WO) . |
| WO 97/02786 | 1/1997 | (WO) . |
| WO 98/34554 | 8/1998 | (WO) . |

*Primary Examiner*—Jeffrey A. Smith
*Assistant Examiner*—Eduardo C. Robert
(74) *Attorney, Agent, or Firm*—Pennie & Edmonds LLP (57) ABSTRACT

The invention relates to a device for connecting a longitudinal rod with a bone anchoring element, such as a pedicle screw, thereby forming a system for fixation of the spine. The device includes a connecting member having upper and lower ends, a bore hole which is open at least towards the lower end and has a central axis, and a through hole positioned perpendicular to the central axis. The device also has a tensioning member insertable in the upper end of the connecting member for securing the bone anchoring element to the connector at a surgeon selected angle. A radially compressible spring chuck is arranged within the connecting member and has a cavity for receiving the head of the bone anchoring element. An insert slides into the bore hole of the connecting member and has a recess with a shape complementary to the outer surface of the spring chuck. The spring chuck is axially supported in the bore hole in such a fashion that radial movement of the spring chuck is not affected.

29 Claims, 7 Drawing Sheets

U.S. PATENT DOCUMENTS

| | | |
|---|---|---|
| 5,578,033 | 11/1996 | Errico et al. . |
| 5,584,834 | 12/1996 | Errico et al. . |
| 5,586,984 | 12/1996 | Errico et al. . |
| 5,591,166 | 1/1997 | Bernhardt et al. . |
| 5,607,426 | 3/1997 | Ralph et al. . |
| 5,609,593 | 3/1997 | Errico et al. . |
| 5,609,594 | 3/1997 | Errico et al. . |
| 5,624,442 * | 4/1997 | Mellinger et al. .................. 606/61 |
| 5,647,873 | 7/1997 | Errico et al. . |
| 5,669,911 | 9/1997 | Errico et al. . |
| 5,672,176 | 9/1997 | Biedermann et al. . |
| 5,681,319 * | 10/1997 | Biedermann et al. .............. 606/61 |
| 5,683,392 | 11/1997 | Richelsoph et al. . |
| 5,688,273 | 11/1997 | Errico et al. . |
| 5,690,630 | 11/1997 | Errico et al. . |
| 5,728,098 | 3/1998 | Sherman et al. . |
| 5,733,285 | 3/1998 | Errico et al. . |
| 5,735,853 | 4/1998 | Olerud . |
| 5,741,255 | 4/1998 | Krag et al. . |
| 5,782,831 | 7/1998 | Sherman et al. . |
| 5,797,911 | 8/1998 | Sherman et al. . |
| 5,810,819 | 9/1998 | Errico et al. . |
| 5,817,094 | 10/1998 | Errico et al. . |
| 5,863,293 | 1/1999 | Richelsoph . |
| 5,879,350 | 3/1999 | Sherman et al. . |
| 6,063,090 | 5/2000 | Schläpfer . |

* cited by examiner

DEVICE FOR CONNECTING A LONGITUDINAL SUPPORT WITH A PEDICLE SCREW

FIELD OF THE INVENTION

The invention relates to a device for the connection of a longitudinal rod with a bone anchoring element.

BACKGROUND OF THE INVENTION

The prior art teaches a number of spinal fixation systems which allow the spinal rod to be inserted after the pedicle screw is implanted with the angle between the rod and pedicle screw variable. An example of such systems is disclosed in European patent 330,881 of Sherman and European patent 441,729 of Vignaud. The disadvantage of these and similar systems is that the rod still must frequently be bent after coupling to the pedicle screw because of anatomical considerations. German patent 19,509,332 of Harms minimizes this disadvantage. Specifically, because relative movement of the screw head with respect to the rest of the screw is possible, the rod need only be bent in one plane after coupling with the pedicle screw.

The disadvantages of this known pedicle screw consist therein that the head part and the threaded part are not apt to be separated, the head part and the longitudinal rod are not apt to be fastened separately with respect to the threaded part, the reachable solidity is low because of the one-sided alignment of the longitudinal slots in the pressure element according to the DE-C 195 09 332 and it is difficult to remobilise the head part once it is fastened. The separability of the head part and the threaded part is a necessity to use different head parts according to the need and that the view is not impeded through the head part during the screwing in of the screw part into the bone. A separate fastening of the head part and the longitudinal rod and a high solidity between head part and threaded part enable the application of distraction and compression without a loss of angle between the pedicle screw and the longitudinal rod and the conservation of the anatomical bending of the stabilized vertebral segments. Remobilization is especially important in case of explantation or new adjustment of the fixation.

A further such connection device is disclosed in WO 97/02786 ERRICO which allows in a simple manner to connect a pedicle screw or more generally a bone anchoring element with a longitudinal rod and which permits a great freedom regarding the angle between the two elements. In case of this known connection device the disadvantage consists therein that the spring chuck is part of the connection element and therefore consists of the same material impairing the choice and pairing of the material with the bone screw to improve the solidity.

SUMMARY OF THE INVENTION

The object of the invention lies therein to provide a device for the connection of a longitudinal rod with a pedicle screw having the following qualities:

simple handling;

screwing in the threaded part of the device even without the connection part;

possible later snap-on of the connection part;

depending on the situation and the preference of the surgeon the free choice of or combination of sidewardly open, upwardly open or closed connection parts. For instance an upwardly open connection part facilitates the insertion of the longitudinal rod while a sideward opening enables sideward corrections and thanks to the possibility of the sideward removing of the connection part each pedicle screw may any time be fastened at the longitudinal rod or be removed again without the necessity of demounting the whole fixation system.

The present invention relates to a vertebral fixation system connector for connecting a longitudinal rod with a bone anchoring element, such as a pedicle screw. The connector includes a connecting member having upper and lower ends, a bore hole through the lower end with a central axis, and a through hole running transversely to the central axis for receiving the longitudinal rod. The connector also has a tensioning member configured and dimensioned for insertion in the upper end of the connecting member for securing the bone anchoring element to the connector at a surgeon selected angle, a radially compressible spring chuck arranged within the connecting member coaxial to the central axis with an upper end and a lower end provided with a cavity for receiving the head of the bone anchoring element, and an insert slidable in the bore hole of the connecting member and having a recess complementary in shape to an outer surface of the spring chuck. The spring chuck is axially supported in the bore hole without impeding radial movement of the spring chuck therein.

The present invention also relates to a vertebral fixation system. The system includes a longitudinal rod, a bone anchoring element, and a connector for connecting the rod to the bone anchoring element. The connector includes a connecting member having upper and lower ends, a bore hole through the lower end with a central axis, and a through hole running transversely to the central axis for receiving the longitudinal rod. The connector also has a tensioning member configured and dimensioned for insertion in the upper end of the connecting member for securing a bone anchoring element having a head and a shaft to the connector at a surgeon selected angle, a radially compressible spring chuck arranged within the connecting member coaxial with the central axis and having an upper end and a lower end that includes a cavity for receiving the head of the bone anchoring element, and an insert slidable in the bore hole of the connecting member and having a recess complementary in shape to an outer surface of the radially compressible spring chuck. The spring chuck is axially supported in the bore hole without impeding radial movement of the spring chuck therein.

The device according to the invention consists of a connection part accepting the longitudinal rod wherein a pedicle screw having a preferably spherical head may afterwards be snapped-on and fastened. The connection part may be simply snapped-on in the desired number and variant onto the pedicle screws already implanted in the vertebral bodies so that a primary connection between longitudinal rod and pedicle screw is produced. Via the screw-in of the tension means into the fixation device the longitudinal rod is axially and rotatively fastened and simultaneously the device is fastened at a stable angle. Thereby the adjusting screw serving as a tension means presses on the longitudinal rod inserted in the device, this one presses on hollow cylinder which encompasses a hollow truncated cone which is alternatingly slotted and radially not fastened and which is itself compressed because of its conically shaped outer surface and wedging the preferably spherical head of the pedicle screw.

The device according to the invention such offers the advantage compared to the known devices that the pedicle screws are not only fastenable exactly perpendicularly to the longitudinal rod but allows an angle of up to ±25° and because of the distance between the rotating center of the connection part and the axis of the longitudinal rod sideward deviations between longitudinal rod and pedicle screw may be compensated to a certain degree depending on the thickness of the longitudinal rod having an amount of between 4 to 10 mm. This qualities enable the application of longitudinal rods standardizedly prebent at the production site what causes serious difficulties by the mounting of conventional systems. A further advantage of a variant of the device according to the invention consists therein that depending on the embodiment of the hollow cylinder and the tension means respectively on the embodiment of the device the longitudinal rod and the preferably spherical head of the bone screw may be fastened separately.

The angular stability may be improved such that the head of the screw consists of a relatively hard material (e.g. Titanium-Aluminium-Niobium-alloy) and the alternately slotted hollow truncated cone consists of a relatively soft material (e.g. Titanium in its soft state).

Another possibility for the improvement of the angular stability consists therein to provide the preferably spherical head of the pedicle screw and/or the complementary cavity in the hollow truncated cone with a three dimensional structure e.g. in the shape of grooves.

Therewith the structure attached at the head of the screw consisting of a relatively hard material is pressed into the relatively soft material of the hollow truncated cone. The change in hardness of the materials may be limited to just in the contact area, too. The difference of hardness may also be obtained through different cold forming or different crystallization of the same material and whereby the harder material is preferably highly trained steel 1.4441 and the soft material is hot treated steel 1.4441. Apart from this the difference of hardness may be obtained via surface treatment as coating or ion implantation.

To be able to screw in the pedicle screws into the bone they are provided at the spherical head preferably with a hexagon socket. If the head apt to be snapped-on is also drilled through optionally only the pedicle screw or the whole device may be screwed in at once. The latter has the advantage above all that at any time the device may be farther screwed in or screwed reverse to obtain a compensation in height.

A further embodiment of the invention consists therein that the angles of the cones of the spring chuck and of the insert compressing the spring chuck are different and form a not self-locking cone joining.

Other embodiments of the device according to the invention enable a subsequent insertion of the longitudinal rod from the side or from above. Through the screw in of the tension screw into the fixation device simultaneously the longitudinal rod is fastened axially and rotatively within the device and the device is fastened at a stable angle. Thereby the tension screw presses onto the longitudinal rod inserted in the device, this one presses onto the insert of the fixation device and this insert wedges the springable contact studs of the spring chuck via a preferably conical shaped inner surface and a corresponding likewise conical shaped outer surface of the spring chuck on the preferably spherical head of the pedicle screw.

BRIEF DESCRIPTION OF THE DRAWINGS

The invention and further embodiments of the invention are discussed in more detail in the following section by means of the partially schematic representations of several embodiments.

The figures show.

DETAILED DESCRIPTION OF THE PREFERRED EMBODIMENTS

Figure 1:
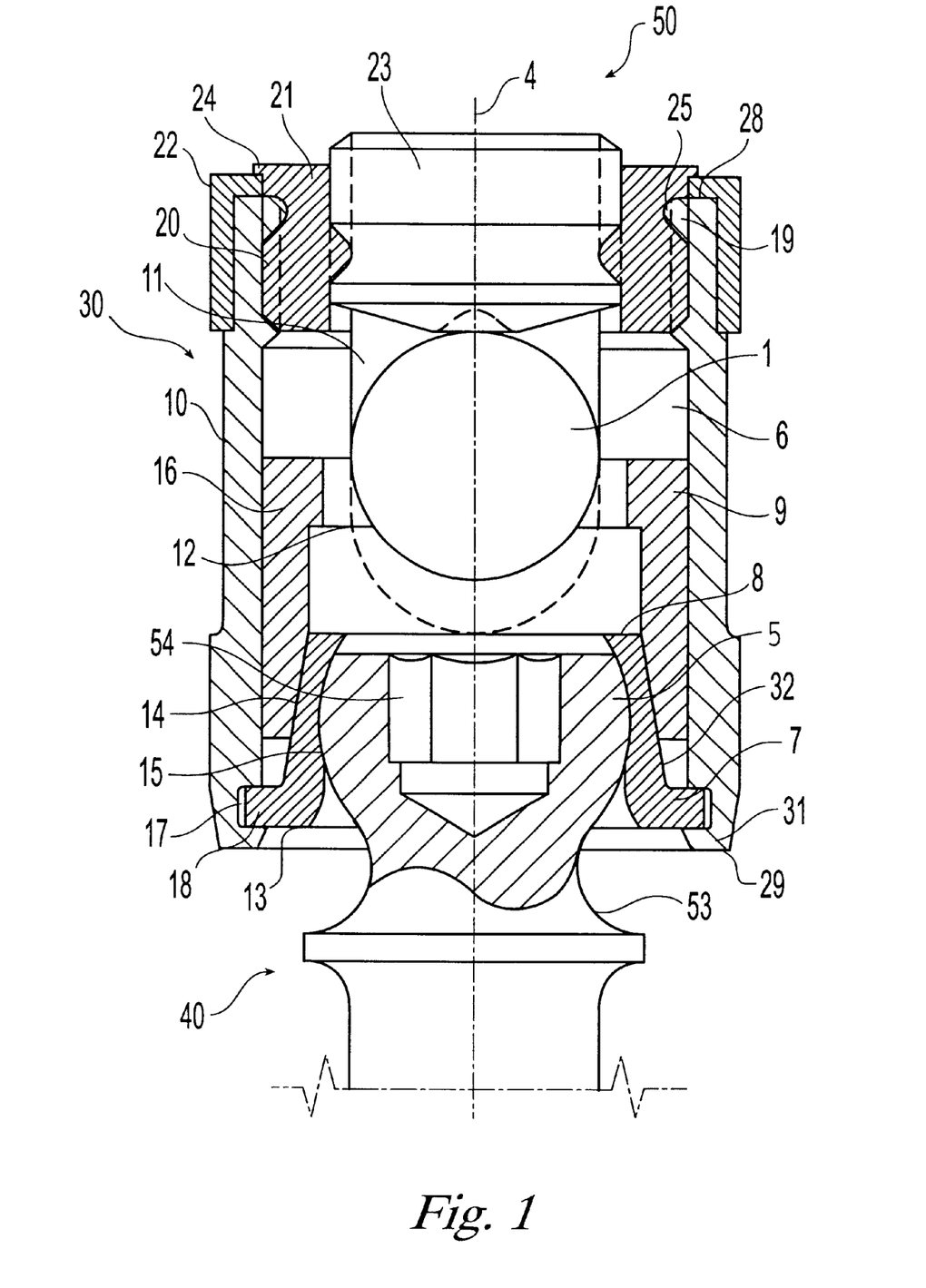
FIG. 1 a longitudinal cut through the connection part of a variant of the device according to the invention together with a longitudinal rod and a pedicle screw having a spherical head.

The variant of the device according to the invention shown in FIG. 1 consists of a hollow cylindrical sleeve 10 which is provided with a channel 11 open towards the upper end 28 for the acceptance of the longitudinal rod 1. If required the channel 11 may also be open towards the side (FIG. 3) or be formed as an oval bore hole (FIG. 4). At the lower end 29 of the sleeve 10 a preferably ring shaped channel 17 is provided wherein the flange 18 of the spring chuck 7 inserted in the bore hole 6 of the sleeve 10 is attachable. Such the spring chuck 7 is fastened against displacement along the central axis 4 of the sleeve 10 but not radially fastened. The spring chuck 7 is provided in its inside with a cavity 15 preferably shaped as a hollow sphere. Slots, wherefrom alternately a first number run into the upper base area 8 and another number run into the lower base area 13 of the spring chuck 7 enable a homogeneous expansion and compression of the spring chuck 7. Thanks to the radial freedom of the spring chuck 7 in the channel 17 the head 5 of the pedicle screw 2 may at any time be snapped into respectively out of the spring chuck 7 as long as the device is not fastened through tightening the tension screw 23. The outside of the spring chuck 7 is shaped tapering conically towards its upper end 8. A hollow cylindrical insert 9 which is shaped complementarily conical to the cone at the spring chuck 7 at its lower end may slide within the bore hole 6 of the sleeve 10 and depending on the effect of force radially compress the spring chuck 7 via the conical joining, 14 and therewith fasten the head 5 of the pedicle screw 2 being inside of the cavity 15. This connection is also loosenable what is facilitated through the attachment of a shoulder 16 in the insert 9. Longitudinal rod 1 and pedicle screw 2 are fastened by means of a tension screw 23 which is screwed in coaxially into an insert screw 21 being at the upper end 28 of the sleeve 10. The tension screw 23 presses when being tightened onto the longitudinal rod 1 which itself presses onto the insert 9 and therewith causes the closure of the spring chuck 7 through pushing into one another the cones 14.

The function of the insert screw consists therein to alter the thread 19 in the sleeve 10 interrupted by the channel 11 into a closed thread wherein the tension screw 23 may run unhindered.

Since the through hole 11 according to the variant of the device according to the invention shown in FIG. 1 is formed as a channel open at the upper end 28 of the sleeve 10 and thus the sleeve 10 is weakened at this part a swivel ring 22 is mounted that prevents the widening of the sleeve 10 when the tension screw 23 is tightened.

Figure 2:
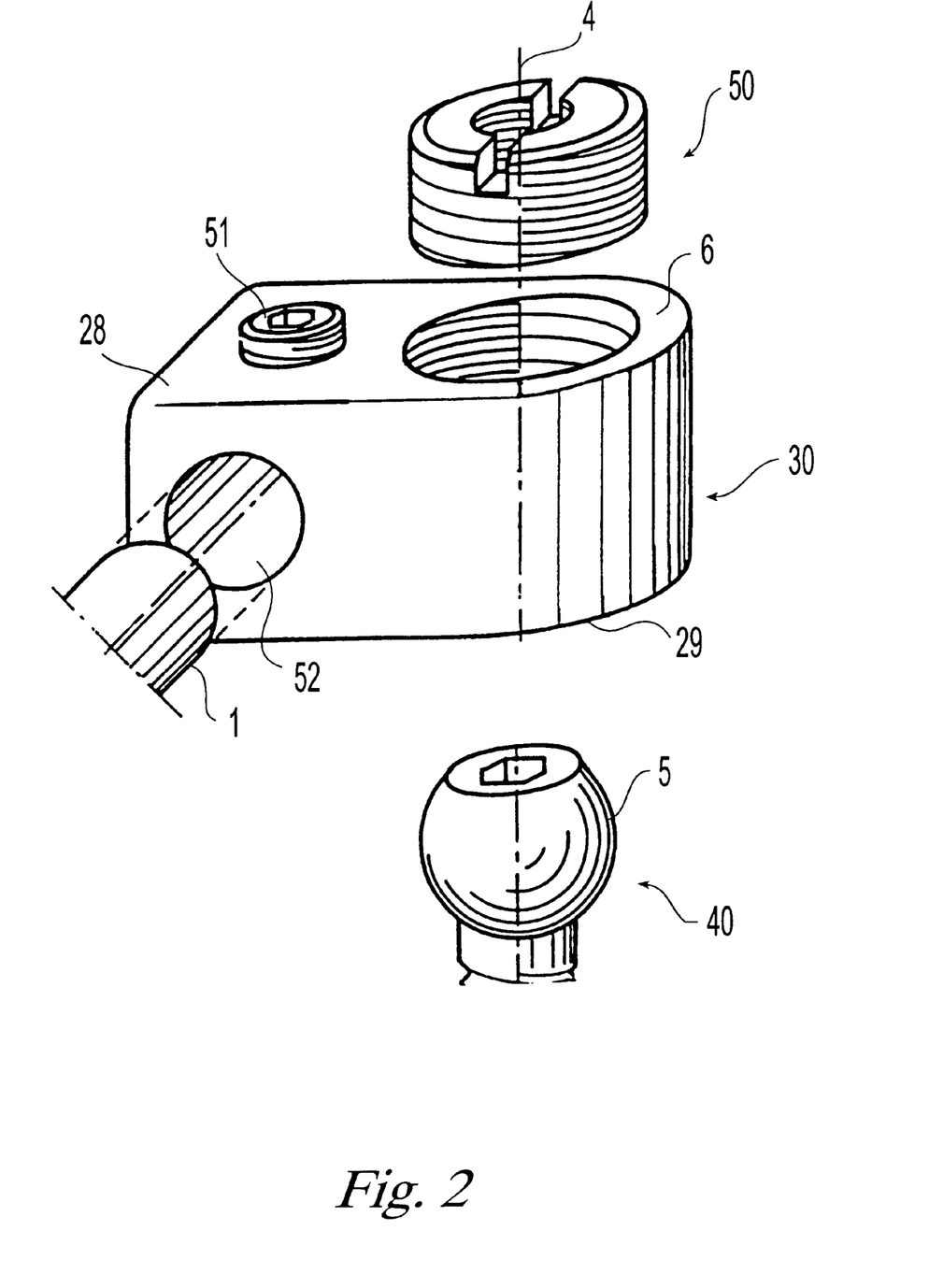
FIG. 2 a perspective representation of a variant of the device according to the invention.

A further variant of the device according to the invention is shown in FIG. 2.

The main difference between the embodiment according to FIG. 1 and the one according to FIG. 2 consists in the sideward dislocation of the channel 52 to the acceptance of the longitudinal rod 1 with respect to the bore hole 6 with the central axis 4. Thus it is possible to separately fasten the longitudinal rod 1 and the pedicle screw 2. From the lower end 29 of the connection part 30 a bone anchoring element 40 may be inserted and be fastened analogously to the variant shown in FIG. 1 by means of a spring chuck 7, an insert 9 and a tension means 50. Thereby the tension means 50 according to the variant shown in FIG. 2 presses directly onto the insert 9. A channel 52 running transversely to the central axis 4 without contacting the bore hole 6 which may again be optionally sidewardly open, open towards the upper end 28 or be realized as a bore hole serves to the acceptance of the longitudinal rod 1. The fastening of the longitudinal rod 1 is done by means of a separate screw 51.

Figure 3:
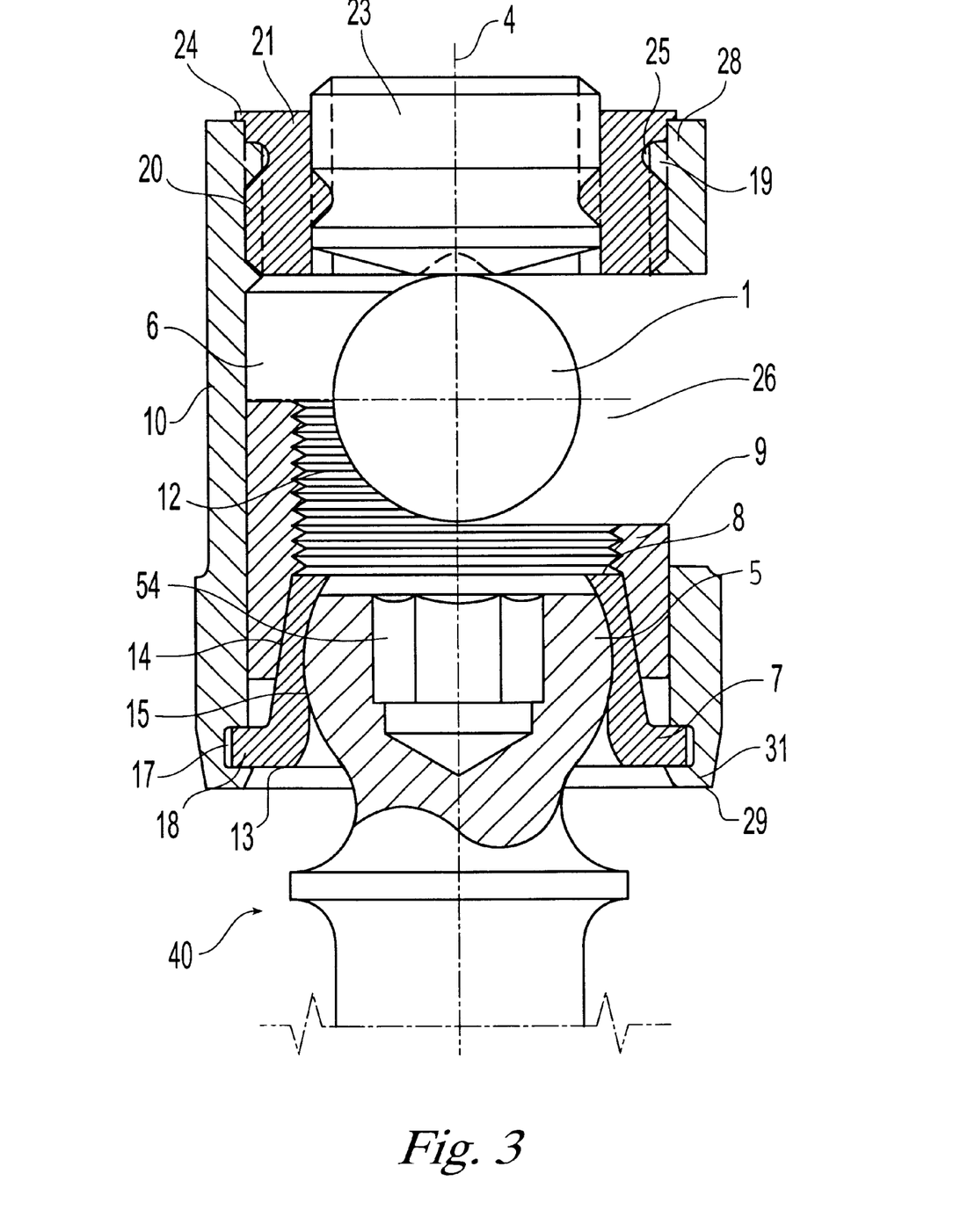
FIG. 3 a longitudinal cut through a modified device according to the invention having qualities as disclosed in FIG. 1 but with the difference that the longitudinal rod is accepted via a sidewardly open channel in the connection part.
Figure 4:
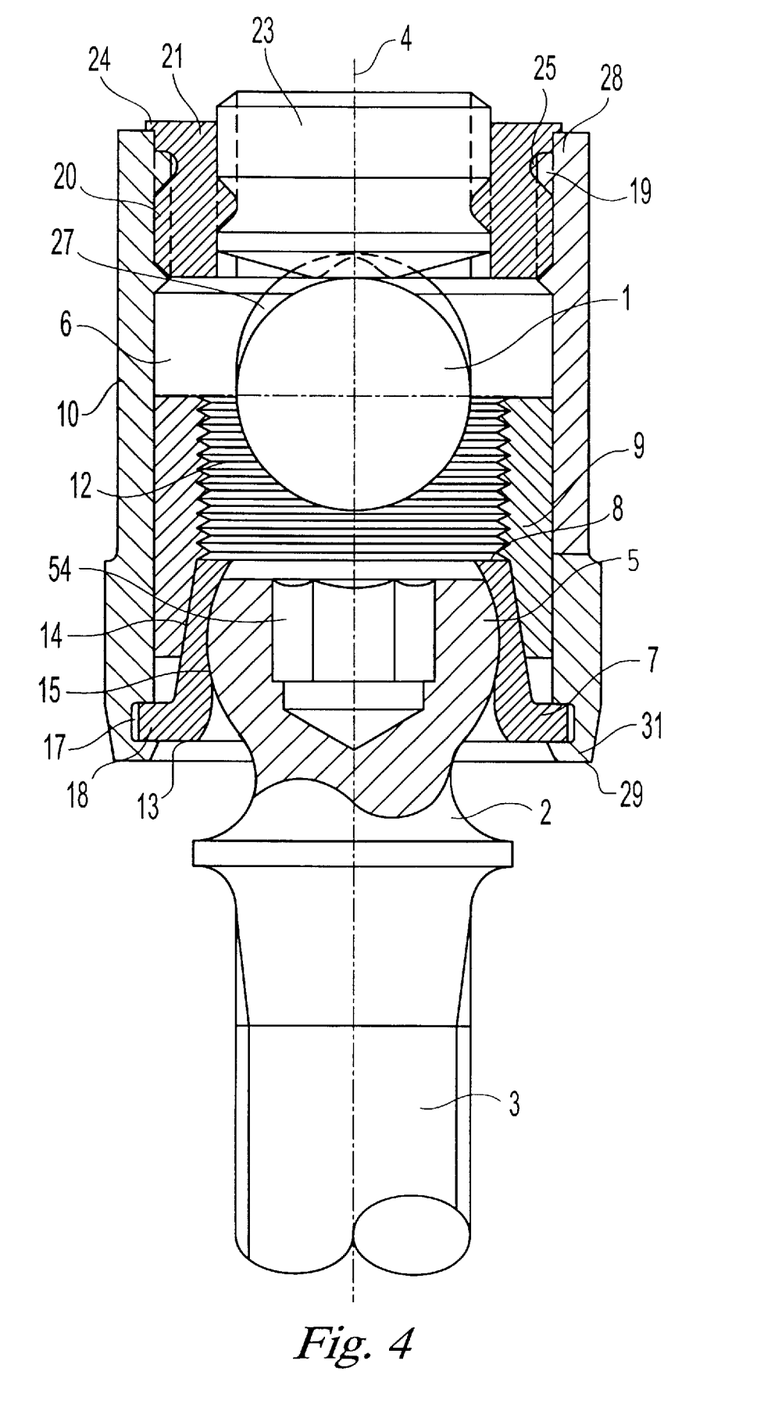
FIG. 4 a longitudinal cut through a modified device according to the invention having qualities as disclosed in FIG. 1 but with the difference that the longitudinal rod is accepted in an oval channel in the connection part.

The variant of the device according to the invention shown in FIG. 3 differentiates from the variant shown in FIG. 1 only by that means that the sidewardly open through opening 26 in the sleeve 10 accepts the longitudinal rod 1. The insert 9 is lower at this side, too. Thus, the longitudinal rod 1 may be subsequently inserted into the device as in case of the variant shown in FIG. 1.

The variant of the device according to the invention shown in FIG. 4 differentiates from the variant shown in FIG. 1 only by that means that a closed oval through opening 27 within the sleeve 10 accepts the longitudinal rod 1.

Figure 5:
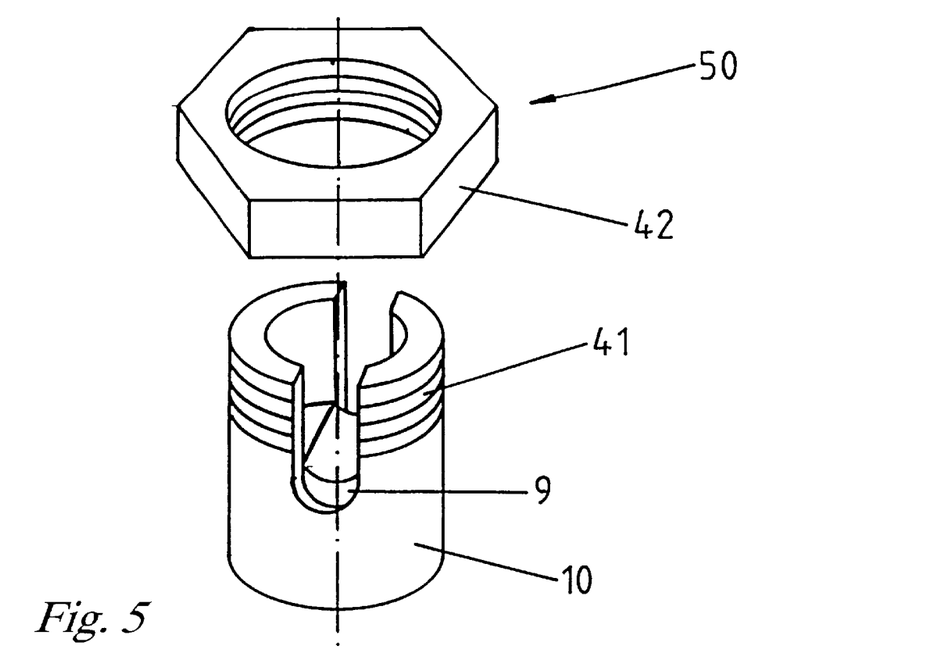
FIG. 5 a perspective representation of a variant of the device according to the invention.

The variant of the device according to the invention shown in FIG. 5 differentiates from the variant shown in FIG. 1 only by that means that a nut 42 is employed as a tension means 50. Thereto the sleeve 10 is provided with an exterior thread 41 whereon the nut 42 is screwed. When tightened the nut 42 presses onto the longitudinal rod 1 which itself presses onto the insert 9 by what means the spring chuck 7 is radially compressed and such the head 5 of the pedicle screw 2 and the longitudinal rod 1 are simultaneously fastened. A collapse of the channel 11 may be prevented by forming the thread 41 as buttress thread or by inserting a cylindrical element 47 Into the bore hole 6.

Figure 6:
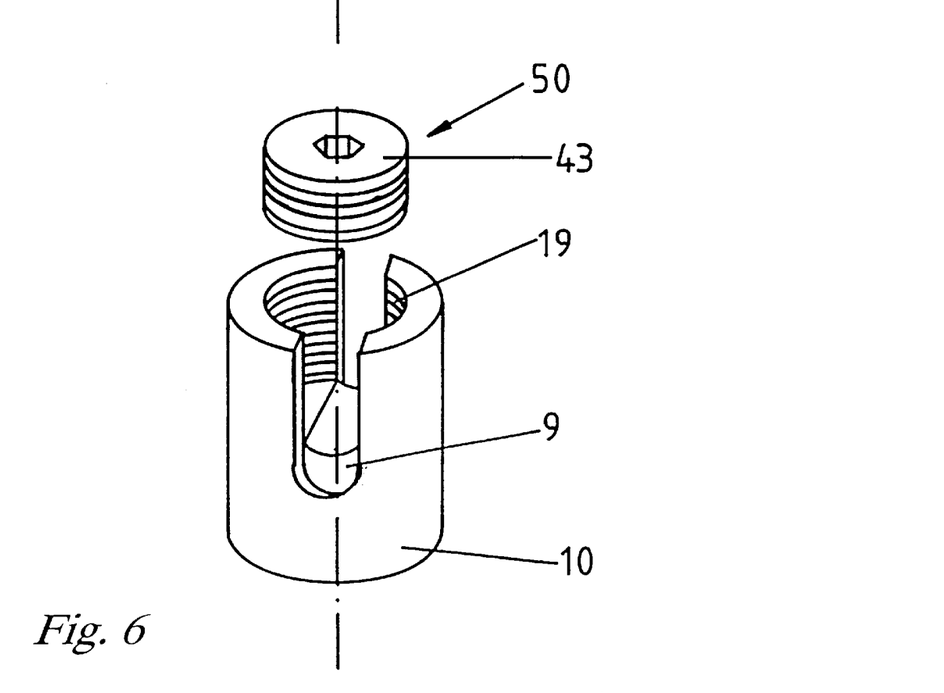
FIG. 6 a perspectival representation of a further variant of the device according to the invention.

In FIG. 6 another variant of the device according to the invention is shown. This one differentiates from the variant shown in FIG. 1 that a locking screw 43 serves as a tension means 50. The widening of the channel 11 is prevented by forming the thread 19 as a buttress thread.

Figure 7:
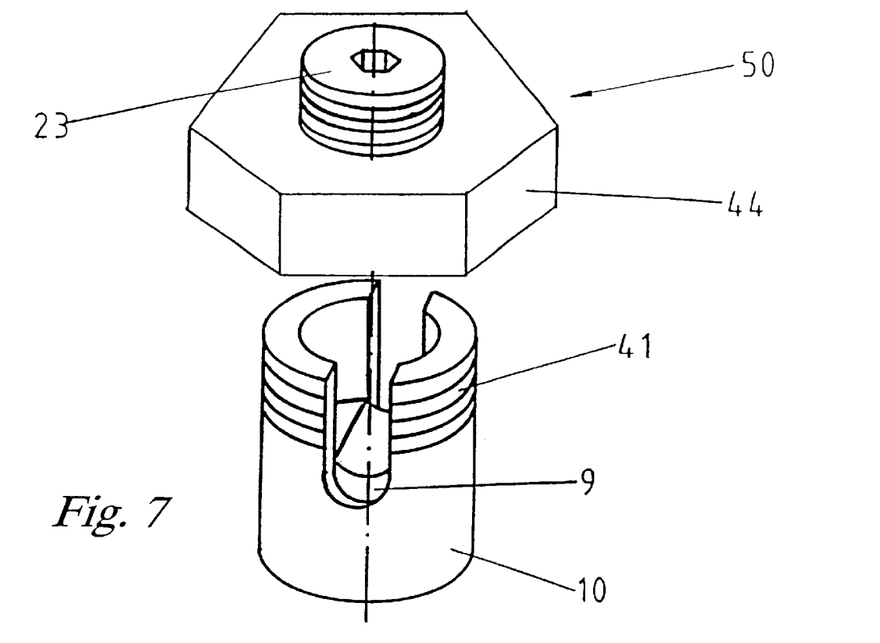
FIG. 7 a perspective representation of a further variant of the device according to the invention.

The variant shown in FIG. 7 differentiates from the variant shown in FIG. 1 through the construction of the tension means 50. The sleeve 10 is provided with an exterior thread 41 whereon the threaded sleeve 44 is screwed. The fastening of the longitudinal rod 1 and pedicle screw 2 happens by means of a tension screw 23 which is screwed into the threaded sleeve 44. The threaded sleeve 44 thus has the same function as the threaded insert 21 shown in FIG. 1. Thanks to the threaded sleeve 44 inserted between the slotted thread 41 and the tension screw 23 the tension screw 23 runs within an uninterrupted thread.

Figure 8:
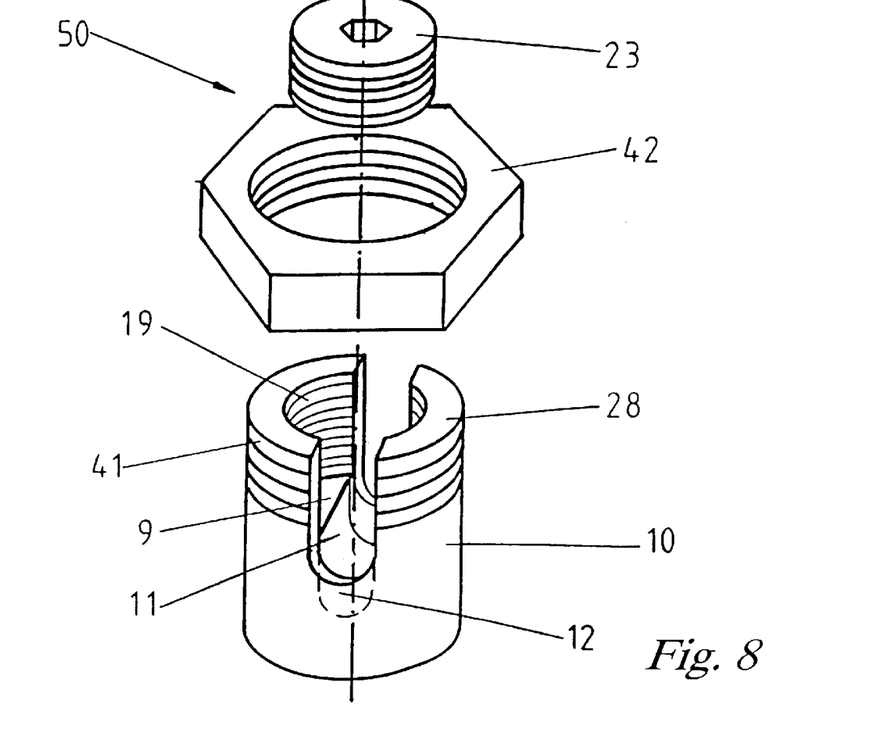
FIG. 8 a perspective representation of a further variant of the device according to the invention.

Another variant of the device according to the invention is shown in FIG. 8. This variant allows the longitudinal rod 1 and the pedicle screw 2 to be fastened separately. To achieve this the sleeve 10 is provided at its upper end 28 with an interior thread 19 and an exterior thread 41. The channel 12 of the insert 9 is shaped such that the longitudinal rod 1 always lies on the lower edge of the through opening 11 during its fastening by means of the nut 42. When the tension screw 23 which presses directly on the insert 9 extending over the longitudinal rod 1 is tightened the spring chuck 7 is compressed thus fastening the pedicle screw 2.

Figure 9:
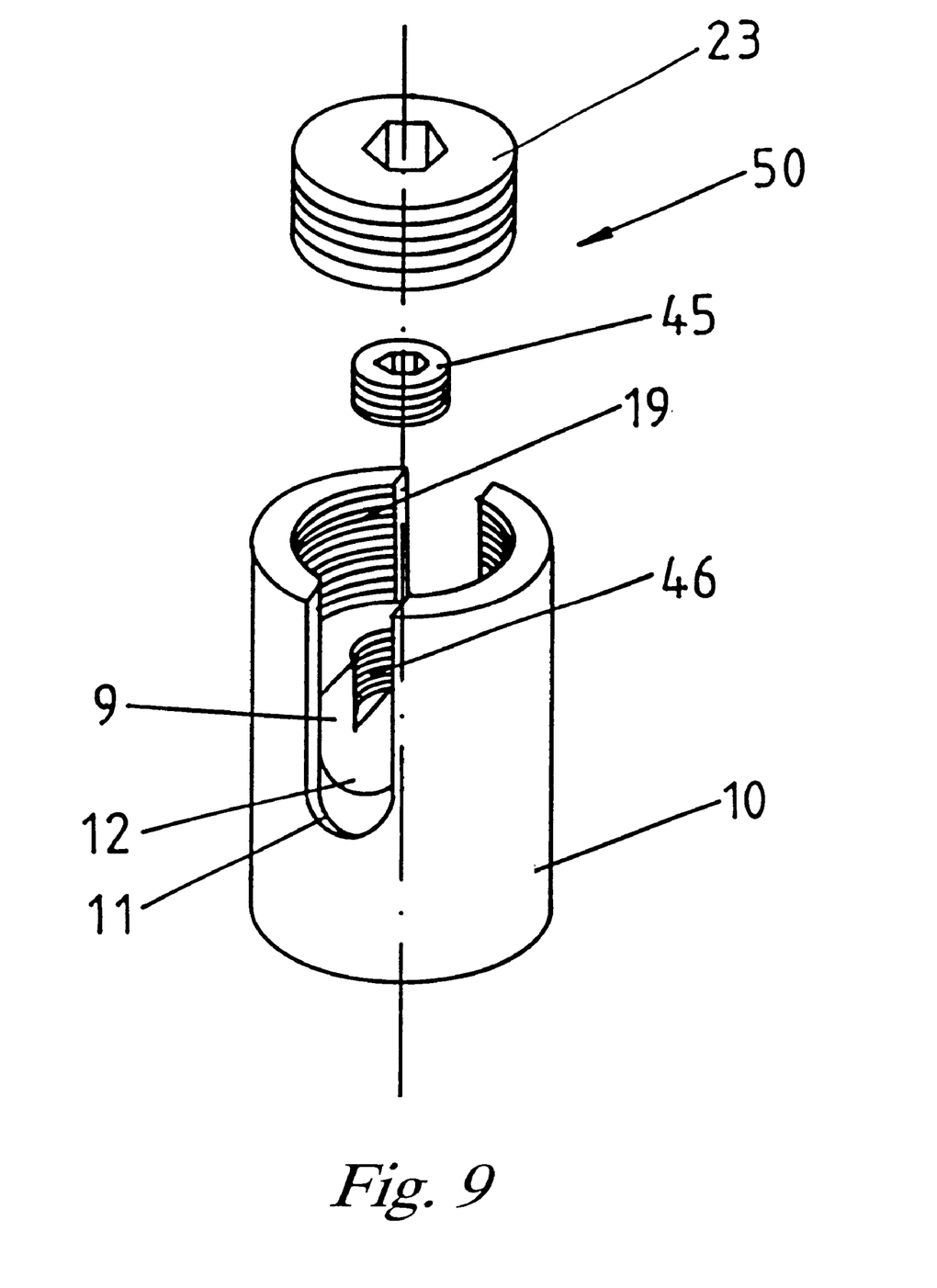
FIG. 9 a perspective representation of a further variant of the device according to the invention.

The variant of the device according to the invention shown in FIG. 9 also enables a separate fastening of the longitudinal rod 1 and the pedicle screw 2. The trough opening 11 and the channel 12 are shaped such that the longitudinal rod 1 always lies on the channel 12 when fastened. The longitudinal rod 1 is fastened by means of a stud bolt 45 which is screwed into an interior thread 46 in the insert 9. The tension screw 23 serves to fasten the pedicle screw 2 whereby the tension screw 23 presses onto the insert 9 whereby this one is sliding over the spring chuck 7 thus radially compressing it. The widening of the channel 11 may also be prevented either by shaping the threads 19 and 46 as buttress threads or by using a sleeve 22 as shown in FIG. 1.

What is claimed is:

1. A vertebral fixation system connector for connecting a longitudinal rod with a bone anchoring element, the connector comprising:

a connecting member having upper and lower ends, a bore hole through the lower end with a central axis, and a through hole running transversely to the central axis for receiving a longitudinal rod;

a tensioning member configured and dimensioned for insertion in the upper end of the connecting member for securing a bone anchoring element having a head and a shaft to the connector at a surgeon selected angle;

a radially compressible spring chuck arranged within the connecting member coaxial with the central axis and having an upper end and a lower end that includes a cavity for receiving the head of the bone anchoring element; and an insert slidable in the bore hole of the connecting member and having a recess complementary in shape to an outer surface of the radially compressible spring chuck, wherein the spring chuck is axially supported in the bore hole without impeding radial movement of the spring chuck therein.

2. The connector of claim 1 wherein the connecting member has a shoulder for supporting the spring chuck in the bore hole.

3. The connector of claim 2 wherein the shoulder has a ring groove.

4. The connector of claim 1 wherein the connecting member is a cylindrical sleeve.

5. The connector of claim 1 wherein the outer surface of the spring chuck and the recess of the insert each have a conical shape.

6. The connector of claim 5 wherein both the outer surface of the spring chuck and the recess have conical angles of at least about 10°, with the angles differing by less than about 1°.

7. The connector of claim 5 wherein both the outer surface of the spring chuck and the recess have conical angles of at least about 10°, with the angles differing by between about 4° and 6°.

8. The connector of claim 1 wherein a sidewall of the connecting device has an opening for receiving the longitudinal rod.

9. The connector of claim 1 herein the through hole has an oval shape.

10. The connector of claim 1 herein the tensioning member includes an insert screw having an external thread and the upper end of the connecting member has an internal thread.

11. The connector of claim 10 wherein the internal thread and external thread are buttress threads.

12. The connector of claim 1 wherein the recess is convexly shaped in an area of contact between the insert and the spring chuck.

13. The connector of claim 1 wherein the upper end of the insert has a ridge for compressing against the spring chuck.

14. The connector of claim 1 wherein the insert has a cylindrical shape.

15. The connector of claim 1 wherein a cross-section of the insert has a polygonal shape.

16. The connector of claim 1 wherein the bore hole and the through hole are connected to each other.

17. The connector of claim 1 wherein the tensioning member provides for simultaneous fixation of the longitudinal rod and the head of the bone anchoring element.

18. The connector of claim 1 wherein the tensioning element is configured and dimensioned to press on the longitudinal rod.

19. The connector of claim 18 wherein the tensioning element comprises a nut and the upper end of the connecting element has an external thread for threadably receiving the nut.

20. The connector of claim 18 wherein the tensioning element comprises a locking screw and the upper end of the connecting element has an internal thread for threadably receiving the locking screw.

21. The connector of claim 1 wherein at least a portion of the insert has an internal thread, and wherein a stud bolt having a shaft with an external thread is threadably received by the insert to press on the longitudinal rod.

22. The connector of claim 1 wherein the cavity of the spring chuck has a spherical shape.

23. The connector of claim 1 wherein the spring chuck has a plurality of slots for allowing the radial movement of the spring chuck, with at least one of the slots extending from the upper end of the spring chuck.

24. A vertebral fixation system comprising:
a longitudinal rod;
a bone anchoring element; and
a connector for connecting the rod to the bone anchoring element, said connector comprising:
a connecting member having upper and lower ends, a bore hole through the lower end with a central axis, and a through hole running transversely to the central axis for receiving the longitudinal rod;
a tensioning member configured and dimensioned for insertion in the upper end of the connecting member for securing a bone anchoring element having a head and a shaft to the connector at a surgeon selected angle;
a radially compressible spring chuck arranged within the connecting member coaxial with the central axis and having an upper end and a lower end that includes a cavity for receiving the head of the bone anchoring element; and
an insert slidable in the bore hole of the connecting member and having a recess complementary in shape to an outer surface of the radially compressible spring chuck, wherein the spring chuck is axially supported in the bore hole without impeding radial movement of the spring chuck therein.

25. The connector of claim 24 wherein the bone anchoring element is a pedicle screw.

26. The connector of claim 24 wherein the bone anchoring element has a turned groove below the head.

27. The connector of claim 24 wherein the spring chuck and the head of the bone anchoring element have different hardnesses in an area of contact between the head and the spring chuck.

28. The connector of claim 27 wherein the harder material is an alloy of Titanium, Aluminum, and Niobium, and the softer material is commercially pure titanium.

29. The connector of claim 27 wherein the head and the spring chuck are made of the same material and the difference in hardness is obtained by surface treatment processing of the material.

* * * * *

UNITED STATES PATENT AND TRADEMARK OFFICE
CERTIFICATE OF CORRECTION

PATENT NO. : 6,248,105 B1
DATED : June 19, 2001
INVENTOR(S) : Fridolin Schläpfer and Martin Hess Page 1 of 1

It is certified that error appears in the above-identified patent and that said Letters Patent is hereby corrected as shown below:

<u>Column 7,</u>
Line 4, replace "herein" with -- wherein --; and
Line 6, replace "herein" with -- wherein --.

Signed and Sealed this

Fifteenth Day of January, 2002

Attest:

JAMES E. ROGAN
*Attesting Officer*     *Director of the United States Patent and Trademark Office*